United States Patent [19]

Schröder

[11] Patent Number: 4,987,232

[45] Date of Patent: Jan. 22, 1991

[54] PREPARATION OF 2-CHLOROPYRIDINE 3-CARBOXYLIC ACID ESTERS

[75] Inventor: Ludwig Schröder, Ingelheim am Rhein, Fed. Rep. of Germany

[73] Assignee: Shell Internationale Research Maatschappij, B.V., The Hague, Netherlands

[21] Appl. No.: 446,135

[22] Filed: Dec. 5, 1989

[30] Foreign Application Priority Data

Dec. 5, 1988 [DE] Fed. Rep. of Germany ....... 3840954

[51] Int. Cl.$^5$ ................. C07D 215/16; C07D 215/12; C07D 211/70
[52] U.S. Cl. ................................... 546/153; 546/154; 546/156; 546/174; 546/298; 546/314
[58] Field of Search ............... 546/153, 154, 156, 174, 546/298, 314

[56] References Cited

FOREIGN PATENT DOCUMENTS 2713316 10/1977 Fed. Rep. of Germany .
80208 11/1971 German Democratic Rep. .
22161 3/1901 Hungary .
33469 1/1905 Hungary .
213760 12/1983 Japan .
144759 8/1984 Japan .

OTHER PUBLICATIONS

J. Org. Chem. 19, 1633, (1954), E. C. Taylor et al., Pyridine-1-Oxides, I. Synthesis of Some Nicotinc Acid Derivatives.

*Primary Examiner*—Mary C. Lee
*Assistant Examiner*—Joseph K. McKane

[57] ABSTRACT

2-chloropyridine 3-carboxylic acid esters are prepared by cyclization of 1,3-butadiene derivatives in the presence of hydrogen chloride.

7 Claims, No Drawings

PREPARATION OF 2-CHLOROPYRIDINE 3-CARBOXYLIC ACID ESTERS

The present invention relates to a process for the preparation of 2-chloropyridine 3-carboxylic acid esters. The esters obtained by the process according to the invention can easily be converted by well known procedures into 2-chloropyridine 3-carboxylic acid acids which are valuable as starting materials for the preparation of various herbicides and fungicides. Examples of such pesticides are disclosed in European published applications Nos. EP 53011 and EP 256503.

Various processes have been described for the preparation of 2-chloronicotinic acid, its nitrile or esters. However, these have not proved to be satisfactory for technical scale production. For example, J. Org. Chem. 19, 1633 (1954) discloses the following process for the preparation of 2-chloronicotinic acid nitrile:

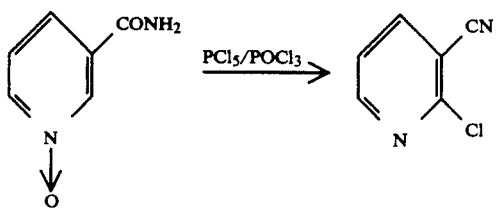

However, the desired product is obtained in only about 35% yield.

East German Patent No. 80.208, Hungarian Patent Nos. 22.161 and 33.469, German Offenlegungsschrift No. P 2713316 and Japanese patent application no. 59-144.759 describe modifications of the above reaction which give improved yields. However, more recent publications, such as Chem. Pharm. Bull. Jpn. 36, 2244 (1988), show that this reaction always yields additional isomers which necessitate difficult and extensive separation processes to obtain the desired product due to the similar chemical and physical properties of the isomers in question.

It is also known from Japanese patent application no. 58-213.760 that 2-chloronicotinic acid can be prepared by saponification of 2-chloro-3-trichloromethyl pyridine. However, the starting material for this process can only be obtained by an extensive multi-step synthesis.

Additionally, it is known from Spanish Patent No. 501.988 that 2-chloro-3-methyl pyridine can be oxidized by a mixture of $H_2SO_4/HNO_3$ at a temperature of about 200° C. to form 2-chloronicotinic acid. However, this process causes corrosion problems and a large amount of highly toxic gases have to be removed when the process is performed on a technical scale.

It is also known from Japanese patent specification no. 80-76.863 that 2-chloronicotinic acid esters can be prepared by the following cyclisation process:

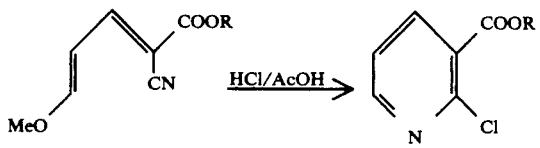

However, the reaction has to be carried out at low temperatures and requires reaction times of about 40 hours.

There is therefore an urgent need for a process which allows the preparation of 2-chloropyridine 3-carboxylic acids or their esters in high yield from cheap starting materials and under easily controllable reaction conditions.

It has now been found that, surprisingly, 2-chloropyridine 3-carboxylic acid esters can be prepared in high yields under mild reaction conditions starting from butadienyl amine derivatives. Accordingly, the present invention provides a process for the preparation of a 2-chloropyridine 3-carboxylic acid ester of the general formula

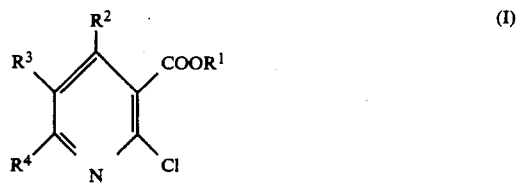

in which $R^1$ represents an optionally substituted alkyl, alkenyl, alkynyl or cycloalkyl group;

$R^2$ represents a hydrogen atom or an optionally substituted alkyl or alkoxy group; and $R^3$ and $R^4$ independently represent a hydrogen atom or an optionally substituted alkyl or alkoxy group or $R^3$ and $R^4$ together represent an optionally substituted alkylene group;

characterised in that a butadiene derivative of the general formula

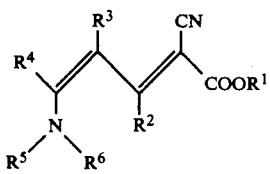

in which $R^1$, $R^2$, $R^3$ and $R^4$ are as defined above and $R^5$ and $R^6$ independently represent a hydrogen atom or an optionally substituted alkyl, alkenyl, alkynyl, cycloalkyl or aryl group or $R^5$ and $R^6$ together with the interjacent nitrogen atom represent an optionally substituted heterocyclic ring, is reacted with hydrogen chloride.

When the compounds of this invention contain an alkyl, alkenyl or alkynyl substituent group, this may be linear or branched and may contain up to 10, preferably up to 6 and especially up to 4, carbon atoms. A cycloalkyl group may contain from 3 to 10, preferably 3 to 6, carbon atoms. An alkylene group may contain 1 to 8, preferably 2 to 6, carbon atoms. An aryl group may be any aromatic hydrocarbon group, especially a phenyl or naphthyl group. A heterocyclic ring may be any saturated or unsaturated ring system containing at least one nitrogen atom and may also contain an additional heteroatom, 5- and 6-membered rings being especially preferred.

When any of the foregoing substituents are designated as being optionally substituted, the substituent groups which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, hydroxyl, cycloalkyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl and alkylamido groups. When any of the foregoing substituents represents or contains an alkyl substituent group, this may be linear or branched and may contain up to 12, preferably up to 6, and especially up to 4, carbon atoms.

It is preferred that $R^1$ represents a $C_{1-10}$ alkyl, $C_{2-10}$ alkenyl or $C_{2-10}$ alkynyl group, each group being optionally substituted by one or more substituents selected from halogen atoms, $C_{1-4}$ alkoxy, phenyl and naphthyl groups; or a $C_{3-10}$ cycloalkyl group optionally substituted by one or more substituents selected from halogen atoms, $C_{1-4}$ alkyl and $C_{1-4}$ alkoxy groups; $R^2$ represents a hydrogen atom or a $C_{1-6}$ alkyl or $C_{1-6}$ alkoxy group, each group being optionally substituted by one or more halogen atoms; $R^3$ and $R^4$ independently represent a hydrogen atom or a $C_{1-6}$ alkyl or $C_{1-6}$ alkoxy group, each group being optionally substituted by one or more halogen atoms, or $R^3$ and $R^4$ together represent an alkylene group $-(CH_2)_n-$, where n is an integer from 1 to 8, optionally substituted by one or more halogen atoms; and $R^5$ and $R^6$ independently represent a hydrogen atom; a $C_{1-10}$ alkyl, $C_{2-10}$ alkenyl or $C_{2-10}$ alkynyl group, each group being optionally substituted by one or more substituents selected from halogen atoms, $C_{1-4}$ alkoxy, phenyl and naphthyl groups; or a $C_{3-10}$ cycloalkyl, phenyl or naphthyl group, each group being optionally substituted by on or more substituents selected from halogen atoms, $C_{1-4}$ alkyl and $C_{1-4}$ alkoxy groups; or $R^5$ and $R^6$ together with the interjacent nitrogen atom represent a 5- or 6- membered heterocyclic ring optionally containing an additional heteroatom and optionally substituted by one or more substituents selected from halogen atoms, $C_{1-4}$ alkyl and $C_{1-4}$ alkoxy groups.

Especially good results are obtained when $R^1$ represents a $C_{1-4}$ alkyl group; $R^2$ represents a hydrogen atom or a $C_{1-4}$ alkyl or $C_{1-4}$ alkoxy group; $R^3$ and $R^4$ independently represent a hydrogen atom or a $C_{1-4}$ alkyl or $C_{1-4}$ alkoxy group or $R^3$ and $R^4$ together represent an alkylene group $-(CH_2)_n-$, where n is an integer from 2 to 6; and $R^5$ and $R^6$ independently represent a hydrogen atom or a $C_{1-4}$ alkyl or phenyl group or $R^5$ and $R^6$ together with the interjacent nitrogen atom represent a 5- or 6-membered heterocyclic ring.

Most preferably, $R^1$ represents a methyl or ethyl group, $R^2$ represents a hydrogen atom, methyl or ethoxy group, $R^3$ and $R^4$ independently represent a hydrogen atom or a methyl group or together represent a group $-(CH_2)_4-$, and $R^5$ and $R^6$ both represent a methyl group or together with the interjacent nitrogen atom represent a pyrrolidine ring.

It is thought that the reaction proceeds according to the following scheme:

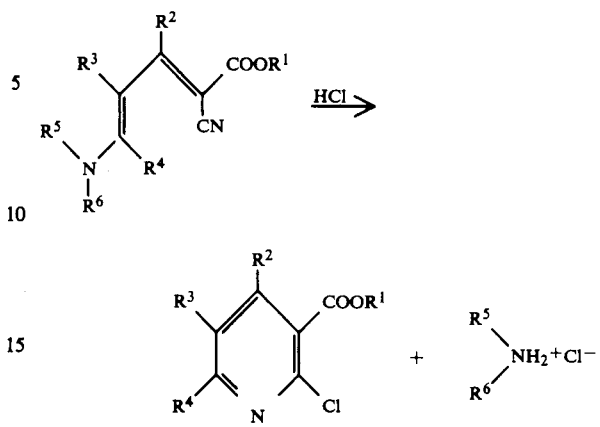

The use of a particular solvent does not appear to be critical and polar, non-polar, protic or aprotic, especially polar or non-polar, solvents can be used, as well as mixtures of these solvents. Suitable solvents include lower alcohols, such as methanol, ethanol, n-propanol, isopropanol, n-butanol or isobutanol, lower ketones, such as acetone or ethyl methyl ketone, chlorinated hydrocarbons, such as dichloromethane or 1,2-dichloroethane, or aromatic hydrocarbons, such as benzene or toluene.

Some of the intermediates of general formula II are known. For instance, the compounds wherein $R^2$ and $R^3$ are hydrogen or alkyl and $R^4$ is hydrogen are described in Collect. Czech. Chem. Commun. 23, 425 (1958) or in J. Org. Chem. 43,2529 (1978).

Compounds of general formula II wherein $R^3$ and $R^4$ together represent an alkylene group may be prepared by methods analogous to those described in, for instance, J. Heterocyclic. Chem. 14, 1077 (1977) according to the following scheme:

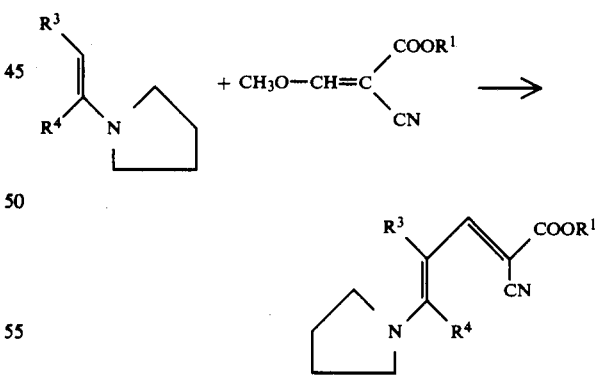

Compounds of general formula II wherein $R_2$ is alkoxy and $R^3$ and $R^4$ are hydrogen may be prepared by methods analogous to those described in Arch. Pharm. 318, 481 (1985) according to the following scheme:

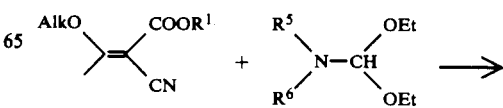

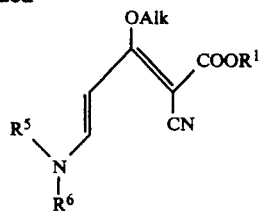

Intermediates of formula II may also be prepared by a process analogous to that described in Collect. Czech. Chem. Commun. 23, 425 (1958). A vinyl ether of formula III

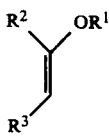

in which $R^1$ to $R^3$ are as hereinbefore defined, is reacted with a dialkylformamide of formula IV

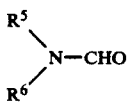

in which $R^5$ and $R^6$ are as hereinbefore defined, and phosgene, trichloromethyl chloroformiate ("diphosgene") or bis(trichloromethyl) carbonate ("triphosgene") in a solvent that is inert under the reaction conditions, for instance, a halogenated hydrocarbon, preferably dichloromethane, 1,2-dichloro- ethane, an ester, such as ethyl acetate, or an aromatic hydrocarbon, such as chlorobenzene. However, the reaction may also be performed without any solvent according9 to DE-A-24 3763. The reaction yields an ammonium compound of formula V

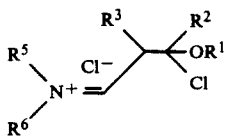

in which $R^1$ to $R^6$ have the meanings given above. After evaporation of the solvent, if necessary, a cyanoacetic acid ester of formula VI

in which $R^1$ is as hereinbefore defined, and a polar solvent, preferably a low aliphatic alcohol, such as methanol, ethanol, n-propanol, isopropanol, n-butanol or isobutanol, are added in a manner analogous to that described in EP No. 57363. The reaction yields intermediates of formula II which may then be cyclised according to the invention to give the desired 2-chloropyridine 3-carboxylic acid esters of formula I.

The preparation of compounds of general formula I may be carried out with isolated intermediates of formula II. However, it is especially advantageous to generate the intermediates in situ and to react them subsequently in a one-pot reaction with hydrogen chloride. The hydrogen chloride may be used in equimolar amounts or in excess, but, it is generally preferred to add it in excess.

The reaction may be conveniently performed at a temperature in the range from 0° C. to 100° C., preferably in the range from 5° C. to 70° C. In practice, a temperature between 10° C. and 50° C. has proved especially suitable.

2-Chloropyridine 3-carboxylic acid esters of formula I may be isolated from the reaction mixture by any of the well established procedures. For example, solvents, such as methanol, and any excess of hydrogen chloride may be removed in vacuo. The residue may then be dissolved in water, the solution neutralised and the subsequently separated ester collected. For further purification, the ester may be distilled in vacuo. However, the crude esters are also suitable as starting materials for further reactions. For instance, the 2-chloropyridine 3-carboxylic acid esters prepared according to the invention can be used for the synthesis of nicotinic acid anilide herbicides such as diflufenican (EP No. 53011).

The process according to the invention is further illustrated by the following examples.

EXAMPLE 1

Preparation of 2-chloronicotinic acid ethyl ester ($R^1=C_2H_5$; $R^2=R^3=R^4=H$)

(i) Preparation of 1-cyano-4-dimethylamino-1-ethoxycarbonyl-1,3-butadiene

3-Dimethylamino-acrolein (99.13g, 1.0 mol), cyanoacetic acid ethyl ester (113.1 g, 1.0 mol), piperidine (4.25 g, 0.05 mol), glacial acetic acid (12g, 0.2 mol) and toluene (1 liter) were boiled with vigorous stirring in a flask equipped with a Dean & Stark apparatus. After 75 minutes the reaction was complete whereby 24 ml to 25 ml of an acetic acid/water mixture were formed. The toluene solution was then cooled with stirring whereupon 1-cyano-4-dimethylamino-1-ethoxycarbonyl-1,3-butadiene precipitated as fine crystalline material. The solvent was removed by vacuum filtration, the product was washed with a small amount of cold toluene and petroleum ether (200 ml) and dried. The yellow, crystalline powder (176.7 g, 91% of theoretical yield) had a m.pt. of 130° C.–132° C. Recrystallisation from a small amount of ethanol gave light yellow crystals with m.pt. 134° C–135° C.

| Elemental analysis ($C_{10}H_{14}N_2O_2$) | | | |
|---|---|---|---|
| calc: | C: 61.83 | H: 7.20 | N: 14.42% |
| found: | C: 61.91 | H: 7.41 | N: 14.31% |

(ii) Preparation of 2-chloronicotinic acid ethyl ester
Method A:

The 1-cyano-4-dimethylamino-1-ethoxycarbonyl-1,3-butadiene (97.1 g, 0.5 mol) obtained in (i) was dissolved in ethanol (400ml) and this solution was saturated with hydrogen chloride whilst stirring. The temperature of the reaction mixture was maintained below 30° C.–35° C. The reaction mixture was stirred for 3 hours at this temperature, then the excess of hydrogen chloride was removed by passing a stream of nitrogen through the solution and the solvent evaporated in vacuo. The resulting gum was dissolved in water and the pH adjusted to 5.0 with aqueous ammonia. The oil separated thereby was collected and the aqueous layer extracted two times with dichloromethane. The organic layers were collected and dried and the solvent was evaporated. Distillation of the resulting oil in water aspirator vacuum yielded a colourless liquid (79.8g, 86% of theoretical yield) with a b.pt.$_{15}$ 140° C.–141° C.

| Elemental analysis ($C_8H_8ClNO_2$): | | | |
|---|---|---|---|
| calc.: | C: 51.76 | H: 4.34 | Cl 19.10 | N 7.55% |
| found: | C: 51.83 | H: 4.50 | Cl 18.95 | N 7.50% |

Method B:

1-Cyano-4-dimethylamino-1-ethoxycarbonyl-1,3-butadiene was reacted with hydrogen chloride as described above except that the ethanolic solution was saturated with hydrogen chloride at 10° C.–15° C. and the mixture was stirred for 4 hours at room temperature (22° C.). Working up according to method A gave 88% of theoretical yield of the desired ester.

EXAMPLE 2

Preparation of 2-chloronicotinic acid ethyl ester (one-pot synthesis) ($R^1=C_2H_5$; $R^2=R^3=R^4=H$)

Method A

N,N-Dimethyl formamide (73g, 1.0 mol) and 1,2-dichloroethane (100 ml) were mixed and a solution of bis(trichloromethyl) carbonate (99 g, 0.33 mol); "triphosgene") in 1,2-dichloroethane (600 ml) was added dropwise over a period of 1 hour (Collect. Czech. Chem. Commun. 23, 425 (1958)). The temperature rose to 30° C.–35° C. and $CO_2$ escaped. The resulting suspension was stirred until gas ceased to be generated (about 90 minutes) and then a mixture of ethylvinyl ether (72 g, 1.0 mol) and 1,2-dichloroethane (100 ml) was added dropwise over a period of 30 minutes. The temperature rose to about 30° C. again. After 1 hour of stirring, the reaction mixture was heated to 70° C. for 15 minutes. The resulting clear solution was evaporated in vacuo whereby a bath temperature of 60° C. was maintained.

The residue was dissolved in ethanol (800 ml) and the resulting solution was stirred, after addition of cyanoacetic acid ethyl ester (85 g, 0.75 mol), for 6 hours under reflux. The reaction solution was then cooled to room temperature, saturated with hydrogen chloride and stirred for another 4 hours at room temperature.

After working up according to Example 1, 2-chloronicotinic acid ethyl ester (113.2g, 61% of theoretical yield with respect to ethylvinyl ether) with a b.pt. $_{15}$ 140° C.–141° C. was obtained.

Method B:

N,N-Dimethyl formamide (73 g, 1.0 mol), vinylisobutyl ether (100 g, 1.0 mol) and phosgene (1 00 g, 1 mol) were reacted at 70° C. in a manner analogous to that described in DE-A-No. 2424373.

The resulting ammonium salt was dissolved hot in ethanol (1.0 liter) and, after addition of cyanoacetic acid ethyl ester (10 1.7 g, 0.9 mol), the mixture was refluxed for 6 hours. The solution was then cooled to 40° C., saturated with hydrogen chloride and stirred for another 2 hours at this temperature.

After working up according to Example 1, 2-chloronicotinic acid ethyl ester (128 g, 69% of theoretical yield with respect to vinyl-isobutylether) with a b.pt.$_{15}$ 138° C.–141° C. was obtained.

EXAMPLE 3

Preparation of 2-chloro-4-ethoxynicotinic acid ethyl ester ($R^1=C_2H_5$; $R^2=C_2H_5O$-; $R^3=R^4=H$)

(i) Preparation of 1-cyano-2-ethoxy-1-ethoxycarbonyl-4-(N,N-dimethylamino)-1,3-butadiene:

1-Cyano-2-ethoxy-1-ethoxycarbonyl-1-propene (22.9 g, 0.125 mol) and N,N-dimethylformamide dimethylacetale in ethanol (100 ml) were stirred under reflux for 2 hours. After cooling, the reaction mixture was evaporated in vacuo. The residual red oil crystallised slowly. 1-Cyano-2-ethoxy-1-ethoxycarbonyl-4-(N,N-dimethylamino)-1,3-butadiene was recrystallised from ethyl acetate yielding orange crystals (19.5 g, 55.7% of theoretical yield) of m.pt. 96° C.–97° C.

| Elemental analysis: ($C_{12}H_{18}N_2O_2$) | | | |
|---|---|---|---|
| calc: | C: 60.48% | H: 7.62% | N: 11.76% |
| found: | C: 60.50% | H: 7.77% | N: 11.69% |

(ii) Preparation of 2-chloro-4-ethoxynicotinic acid ethyl ester

The 1-cyano-2-ethoxy-1-ethoxycarbonyl-4-(N,N-dimethylamino)-1,3-butadiene obtained in (i) in 1,2-dichloroethane (25o ml) was heated to 50° C. with stirring. Simultaneously, a steady stream of hydrogen chloride was passed through the solution for 2 hours. The reaction mixture was then cooled and extracted with water (250 ml). The aqueous layer was extracted with 1,2-dichloroethane and the collected organic layers were washed with water (3×100 ml). The organic layer was then dried with sodium sulphate and concentrated. The residue was distilled in vacuo yielding a yellowish oil (19.5 g, 84.9% of theoretical yield) of bp.$_{0.2\ Torr}$ 131° C.–133° C.

| Elemental analysis ($C_{10}H_{12}ClNO_3$): | | | |
|---|---|---|---|
| calc: | C: 52.29% | H: 5.27% | N: 6.10% | Cl: 15.44% |
| found: | C: 52.26% | H: 5.31% | N: 6.32% | Cl: 15.40% |

EXAMPLE 4

Preparation of 2-chloro-5-methylnicotinic acid methyl ester ($R^1=CH_3$; $R^2=R^4=H$; $R^3=CH_3$)

1-Cyano-4-(N,N-dimethylamino)-1-methoxycarbonyl-3-methyl-1,3-butadiene (33.6 g, 0.173 mol) prepared in a manner analogous to that described in Example 1(i) above was suspended in 1,2-dichloroethane (330 ml) and heated to 50° C. with stirring whereupon a steady stream of hydrogen chloride was passed through the mixture. After 2¼ hours, the clear solution was concentrated. The residue was dissolved in water and this solution was extracted with dichloromethane (3×100 ml). The pooled organic layers were dried with sodium sulphate and evaporated. Crystallisation of the residue from petrol yielded colourless crystals of 2-chloro-5-methylnicotinic acid methyl ester (30.0g, 93.4% of theoretical yield) with m.pt. 31° C.–33° C.

| Elemental analysis ($C_8H_8ClNO_2$): | | | |
|---|---|---|---|
| calc: | C: 51.76% | H: 4.34% | N: 7.55% |
| found: | C: 51.98% | H: 4.50% | N: 7.77% |

EXAMPLE 5

Preparation of 2-chloro-4-methylnicotinic acid ethyl ester ($R^1 = C_2H_5$; $R^2 = CH_3$, $R^3 = R^4 = H$)

1-Cyano-4-(N,N-dimethylamino)-1-ethoxycarbonyl-2-methyl-1,3-butadiene (25.0 g, 0.12 mol) prepared in a manner analogous to that described in Example (i) above in toluene (250 ml) was heated to 50° C. for 3 hours with stirring whereupon a steady stream of hydrogen chloride was passed through the reaction mixture. After cooling, the mixture was washed with water (250 ml). The aqueous layer was then extracted with toluene (3×100 ml). The pooled organic layers were dried with sodium sulphate and evaporated. Distillation of the residue in high vacuo yielded 2-chloro-4-methylnicotinic acid ethyl ester as colourless oil (15.3 g, 64% of theoretical yield) with b.pt.$_{0.04\ Torr}$ 97° C.–98° C.

| Elemental analysis ($C_9H_{10}ClNO_2$): | | | |
|---|---|---|---|
| calc: | C: 54.10% | H: 5.00% | N: 7.01% |
| found: | C: 54.36% | H: 5.21% | N: 6.92% |

EXAMPLE 6

Preparation of 2-chloro-3-methoxycarbonyl-5,6,7,8-tetrahydroquinoline: ($R^1 = CH_3$; $R^2 = H$; $R^3 + R^4 = -(CH_2)_4-$)

(i) Preparation of 1-cyano-1-methoxycarbonyl-2-(2-pyrrolidino-cyclohexenyl)-ethene:

1-Cyano-2methoxy-1-methoxycarbonyl-ethene (8.5 g, 0.06 mol) in tetrahydrofuran (60 ml) was chilled to −25° C. At this temperature, a solution of 1-pyrrolidino-hexene (9.1 g, 0.06 mol) in tetrahydrofuran (30 ml) was added dropwise. Cooling was then stopped and the reaction mixture was allowed to warm up to room temperature. The solution was then stirred for 1 hour and then evaporated. The resulting gum was triturated with isopropanol and the resulting solid material collected by vacuum filtration. After drying, yellowish crystals of 1-cyano-1-methoxycarbonyl-2-(2-pyrrolidino-cyclohexenyl)-ethene (9.5 g, 60.9% of theoretical yield; m.pt. 133° C.–134° C.) Were obtained. The compound migrated in tlc uniformly and was used for the next step without further purification.

(ii) Preparation of 2-chloro-3-methoxycarbonyl-5,6,-7,8-tetrahydroquinoline:

The 1-cyano-1-methoxycarbonyl-2-(2-pyrrolidino-cyclohexenyl)-ethene (9.5 g, 0.036 mol) obtained in (i) was dissolved in 1,2-dichloroethane and a steady stream of hydrogen chloride was passed through the stirred solution. Thereby, the temperature rose to 30° C. The temperature was increased to 50° C. and the reaction mixture was stirred for another 2 hours. After the solution was washed with water and the aqueous layer extracted with 1,2-dichloroethane (3×100 ml). The pooled organic layers were dried with sodium sulphate and evaporated to dryness. The crystalline residue was recrystallised from isopropanol yielding yellow crystals of 2-chloro-3-methoxycarbonyl-5,6,7,8-tetrahydroquinoline (4.8 g, 59.1% of theoretical yield) with 5 m.pt. 80° C.–81° C.

| Elemental analysis ($C_{11}H_{12}ClNO_2$): | | | |
|---|---|---|---|
| calc: | C: 58.54% | H: 5.36% | N: 6.21% |
| found: | C: 58.38% | H: 5.31% | N: 6.25% |

I claim:

1. A process for the preparation of a 2-chloropyridine 3-carboxylic acid ester for the formula:

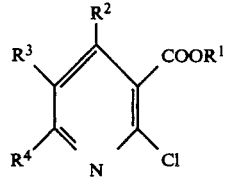

(I)

in which $R^1$ represents a $C_{1-10}$ alkyl, a $C_{2-10}$ alkenyl or $C_{2-10}$ alkynyl group, each group being optionally substituted by one or more substituents selected from halogen atoms, a $C_{1-4}$ alkoxy, phenyl and napthyl groups; or a $C_{3-10}$ cycloalkyl group optionally substituted by one or more substituents selected from halogen atoms, $C_{1-4}$ alkyl and $C_{1-4}$ alkoxy groups;

$R^2$ represents a hydrogen atom or a $C_{1-6}$ alkyl or $C_{1-6}$ alkoxy group, each group being optionally substituted by one or more halogen atoms;

$R^3$ and $R^4$ independently represent a hydrogen atom or a $C_{1-6}$ alkyl or $C_{1-6}$ alkoxy group, each group being optionally substituted by one or more halogen atoms, or $R^3$ and $R^4$ together represent an alkylene group —$(CH_2)_n$—, where n is an integer from 1 to 8, optionally substituted by one or more halogen atoms;

said process comprising the steps of reacting hydrogen chloride with a butadiene derivative of the formula:

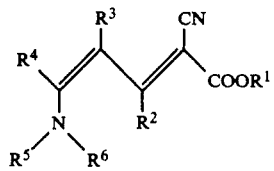

(II)

in which $R^1$, $R^2$, $R^3$ and $R^4$ are as defined above and $R^5$ and $R^6$ independently represent a hydrogen atom, a $C_{1-10}$ alkyl, $C_{2-10}$ alkenyl, or $C_{2-10}$ alkynyl group, each group being optionally substituted by one or more substituents selected from halogen atoms, $C_{1-4}$ alkoxy, phenyl, and naphthyl groups; or a $C_{3-10}$ cycloalkyl, phenyl or naphthyl group, each group being optionally substituted by one or more substituents selected from halogen atoms, $C_{1-4}$ alkyl and $C_{1-4}$ alkoxy groups; or $R^5$ and $R^6$ together with the interjacent nitrogen atom represent a 5- or 6-membered heterocyclic ring optionally substituted by one or more substituents selected from halogen atoms, $C_{1-4}$ alkyl and $C_{1-4}$ alkoxy groups.

2. A process according to claim 1 wherein $R^1$ represents a $C_{1-4}$ alkyl group;

$R^2$ represents a hydrogen atom or a $C_{1-4}$ alkyl or $C_{1-4}$ alkoxy group;

$R^3$ and $R^4$ independently represent a hydrogen atom or a $C_{1-4}$ alkyl or $C_{1-4}$ alkoxy group or $R^3$ and $R^4$ together represent an alkylene group —$(CH_2)_n$—, where n is an integer from 2 to 6; and $R^5$ and $R^6$ independently represent a hydrogen atom or a $C_{1-4}$ alkyl or phenyl group or $R^5$ and $R^6$ together with the interjacent nitrogen atom represent a 5- or 6-membered heterocyclic ring.

3. A process according to any claim 1 wherein the reaction is carried out in the presence of a polar or non-polar solvent.

4. A process according to claim 3 wherein the solvent is selected from methanol, ethanol, n-propanol, isopropanol, n-butanol and isobutanol.

5. A process according to claim 1 wherein the compound of formula II is generated in situ.

6. A process according to claim 1 wherein the reaction is carried out in the presence of an excess of hydrogen chloride.

7. A process according to claim 1 wherein the reaction is carried out at a temperature in the range of from 0° C. to 100° C.

* * * * *